United States Patent
Omata

(10) Patent No.: US 6,959,614 B2
(45) Date of Patent: Nov. 1, 2005

(54) APPARATUS FOR CONTROLLING MOVEMENT OF SPECIMEN, METHOD FOR CONTROLLING MOVEMENT OF SPECIMEN, AND METHOD FOR PROCESSING SPECIMEN

(75) Inventor: Sadao Omata, Koriyama (JP)

(73) Assignee: School Juridical Person Nihon University, Tokyo (JP)

( * ) Notice: Subject to any disclaimer, the term of this patent is extended or adjusted under 35 U.S.C. 154(b) by 356 days.

(21) Appl. No.: 10/221,744
(22) PCT Filed: Mar. 28, 2001
(86) PCT No.: PCT/JP01/02572
§ 371 (c)(1),
(2), (4) Date: Sep. 16, 2002
(87) PCT Pub. No.: WO01/72951
PCT Pub. Date: Oct. 4, 2001

(65) Prior Publication Data
US 2003/0077815 A1 Apr. 24, 2003

(30) Foreign Application Priority Data
Mar. 28, 2000 (JP) .......................................... 2000-88420

(51) Int. Cl.$^7$ ............................................... G01N 1/00
(52) U.S. Cl. ...................................................... 73/863
(58) Field of Search ........................ 73/662, 663, 664, 73/665, 666, 667, 668, 669, 670, 671, 672, 863

(56) References Cited

U.S. PATENT DOCUMENTS

| 5,153,611 | A | * | 10/1992 | Kokado et al. ............... 347/55 |
| 5,512,745 | A |   | 4/1996  | Finer et al. |
| 5,935,143 | A | * | 8/1999  | Hood ......................... 606/169 |
| 6,273,262 | B1 | * | 8/2001 | Yasuda et al. ................. 209/1 |

FOREIGN PATENT DOCUMENTS

JP          A 8-110292          4/1996

OTHER PUBLICATIONS

Omata, "Development of Control System to move and Rotate a Cell and its Stiffness Measurement using a New Tactile Sensor", Nippon Kikai Gakkai Tohoku Shibu Yonezawa Chiho Kouenkai Kouen Ronbunshuu, pp. 197–198, 1999.

* cited by examiner

Primary Examiner—Robert Raevis
(74) Attorney, Agent, or Firm—Oliff & Berridge, PLC

(57) ABSTRACT

An apparatus for controlling the movement of a specimen in order to handle the specimen, e.g., a cell, easily and quickly with high accuracy. A standing wave vibration (V) having at least one node (N1, N2) is generated in a vibrator (11). A specimen in a medium (30) is captured at a position in the vicinity of the surface of the node (N1, N2) and then turned in this position. The capturing position of the specimen (S) is altered through variable control of the vibration mode of the standing wave vibration (V), and the moving route, moving speed, or rotational speed of the specimen (S) is controlled as desired through variable control of the vibration parameters (e.g., frequency, amplitude, intermittent frequency) of the standing wave vibration (V).

5 Claims, 6 Drawing Sheets

APPARATUS FOR CONTROLLING MOVEMENT OF SPECIMEN, METHOD FOR CONTROLLING MOVEMENT OF SPECIMEN, AND METHOD FOR PROCESSING SPECIMEN

TECHNICAL FIELD

The present invention relates to a technology of controlling the movement of a specimen, and especially a small specimen such as a cell, when it is inspected or subjected to a prescribed treatment.

BACKGROUND ART

Various manipulations of a small specimen such as a cell are troublesome operations requiring delicate manipulation with a microtool. One example of such a manipulation is microinjection in a genetic transformation technology. In this genetic engineering technique, a host cell is pricked with an ultrathin glass tube so to introduce recombinant DNA. Introduction of recombinant DNA into a host cell using microinjection will next be described.

The host cell as a specimen is introduced to physiological saline in a petri dish. An operator (worker) uses suction to hold the host cell to the tip of a suction pipette, pricks a nucleus of the held host cell with an ultrathin glass tube, and introduces the recombinant DNA into the nucleus through the glass tube. While performing this operation, the operator uses a microscope to observe the procedure and ascertain that positions are correct.

However, because the host cell, which is in a natural orientation in the physiological saline, is suctioned and held without reorientation at the tip of the pipette by the above operation, when the nucleus is not on the side of the glass tube, in other words when the held specimen does not have a orientation suitable for manipulation, the operator must change the direction of the suction pipette to the specimen repeat the operation of suctioning and holding the specimen. Thus, the operator must take considerable time and trouble to obtain a desired orientation. Further, to capture a desired specimen by this manipulation, it is necessary to move the suction pipette closer to the specimen. In other words, this manipulation involves a great deal of effort requiring experience while observing under a microscope to obtain the desired orientation of a particular specimen.

DISCLOSURE OF THE INVENTION

The apparatus for controlling the movement of a specimen according to the present invention comprises a vibrator which vibrates in a medium, an oscillation mechanism which causes the vibrator vibrate, and a vibration control mechanism which controls the oscillation mechanism so as to cause the vibrator generate a standing wave vibration having at least one node. By configuring as described above, the specimen can be reliably captured at the node of the standing wave vibration in the vicinity of the surface of the vibrator and turned in this position such that the orientation of the specimen can be controlled as desired. Therefore, the instances wherein the complicated procedure described above would be required can be decreased or even eliminated, and the movement of the specimen can be controlled more easily, quicker, and with a higher accuracy.

The apparatus for controlling the movement of a specimen according to the present invention further comprises a vibration mode variable mechanism which can vary a vibration mode of the vibrator. Thus, the position of the node for capturing the specimen can be changed freely, and the specimen can be more accurately moved to a desired position.

When the vibrator is vibrated continuously, the specimen, especially for certain specimens or media, may become damaged or it may become difficult to control the specimens, because the rate of change of movement (e.g., a moving speed or rotational speed) of a specimen becomes high. According to the present invention, the vibration of the vibrator can be switched intermittently to appropriately adjust the vibration energy of the vibrator. Thus, instances of damage to the specimen are decreased, and the rate of change of movement of the specimen is adjusted appropriately, so that the movement of the specimen can be controlled more easily, quicker, and with a high accuracy.

The method for controlling the movement of a specimen according to the present invention comprises a step which places the specimen in a medium and a step which causes a vibrator disposed in the medium to generate a standing wave vibration having at least one node so to capture the specimen at the node of the standing wave vibration in the vicinity of the surface of the vibrator. Thus, the instances wherein the complicated procedure described above would be required can be decreased or even eliminated, and the movement of the specimen can be controlled more easily, quicker, and with a higher accuracy.

The method for manipulating a specimen according to the present invention comprises a step which places the specimen in a medium; a step which causes a vibrator disposed in the medium to generate a standing wave vibration having at least one node so to capture the specimen by the node of the standing wave vibration in the vicinity of the surface of the vibrator; and a step which performs a prescribed treatment of the captured specimen. Thus, the specimen which is accurately captured in a desired position and/or orientation can be treated, so that the prescribed treatment of the specimen can be performed more easily, quicker, and with a high accuracy.

BEST MODE FOR CARRYING OUT THE INVENTION

Figure 1:
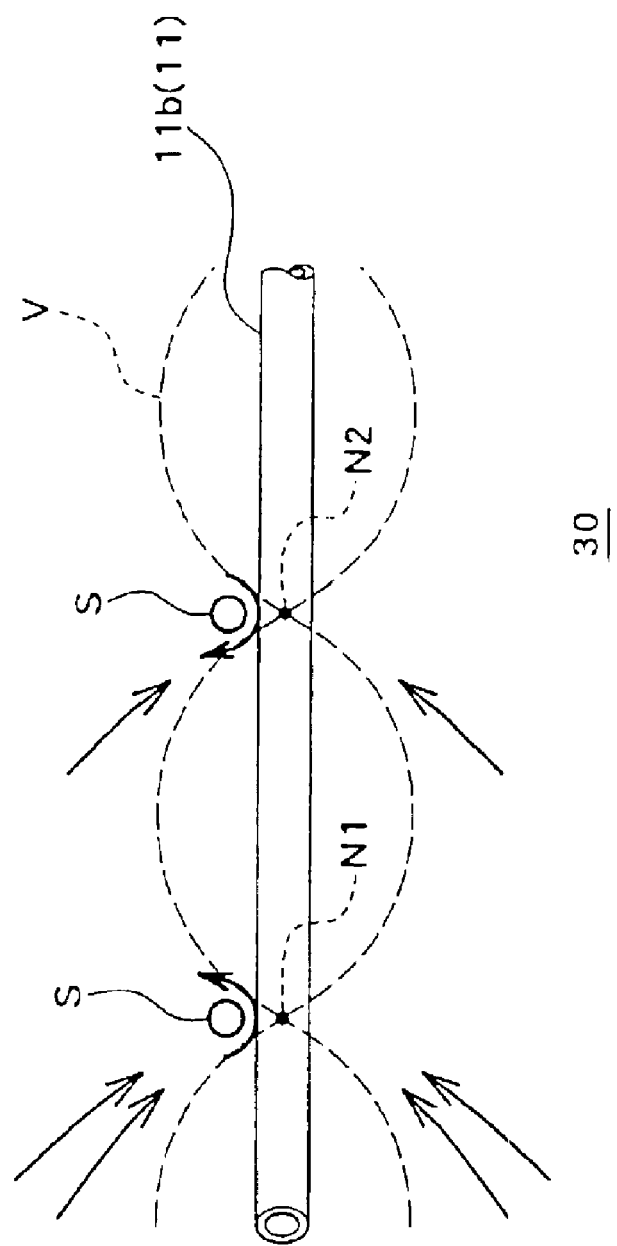
FIG. 1 is an explanatory diagram showing a standing wave vibration of a vibrator of an apparatus for controlling the movement of specimens according to an embodiment of the present invention, and the resulting flow of the mediums and movement of the specimens.
Figure 2:
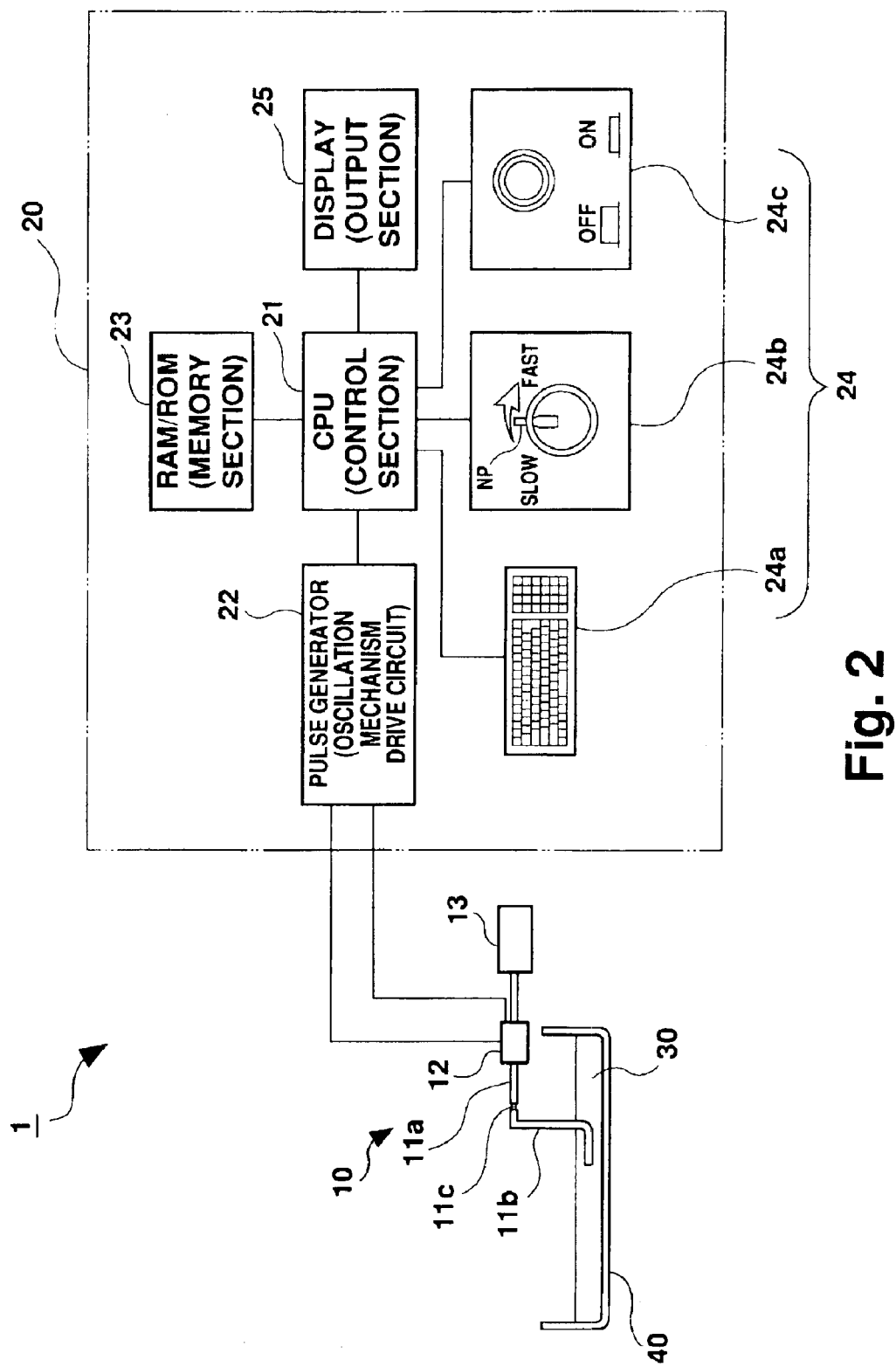
FIG. 2 is a schematic configuration diagram of an apparatus for controlling the movement of a specimen according to the embodiment of the present invention.
Figure 3:
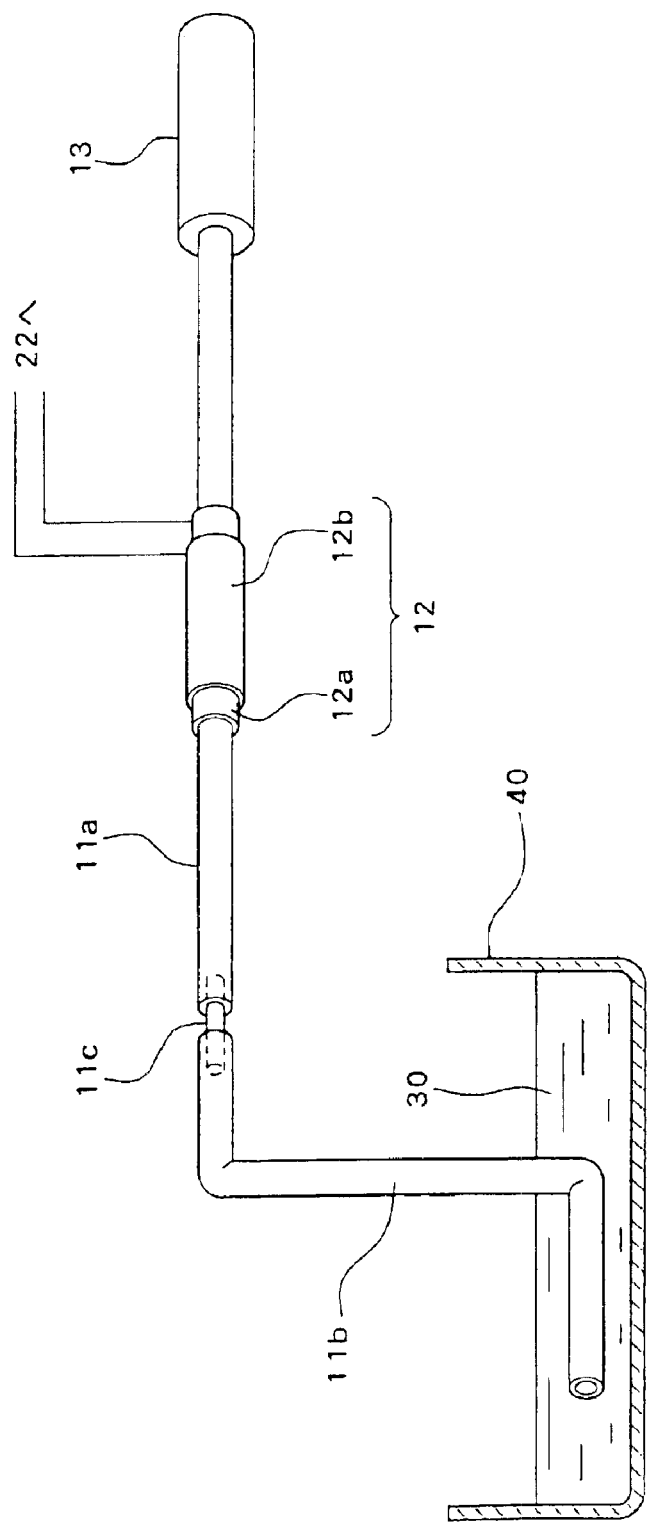
FIG. 3 is a schematic configuration diagram of a manipulator of the apparatus for controlling the movement of a specimen according to the embodiment of the present invention.
Figure 4A:
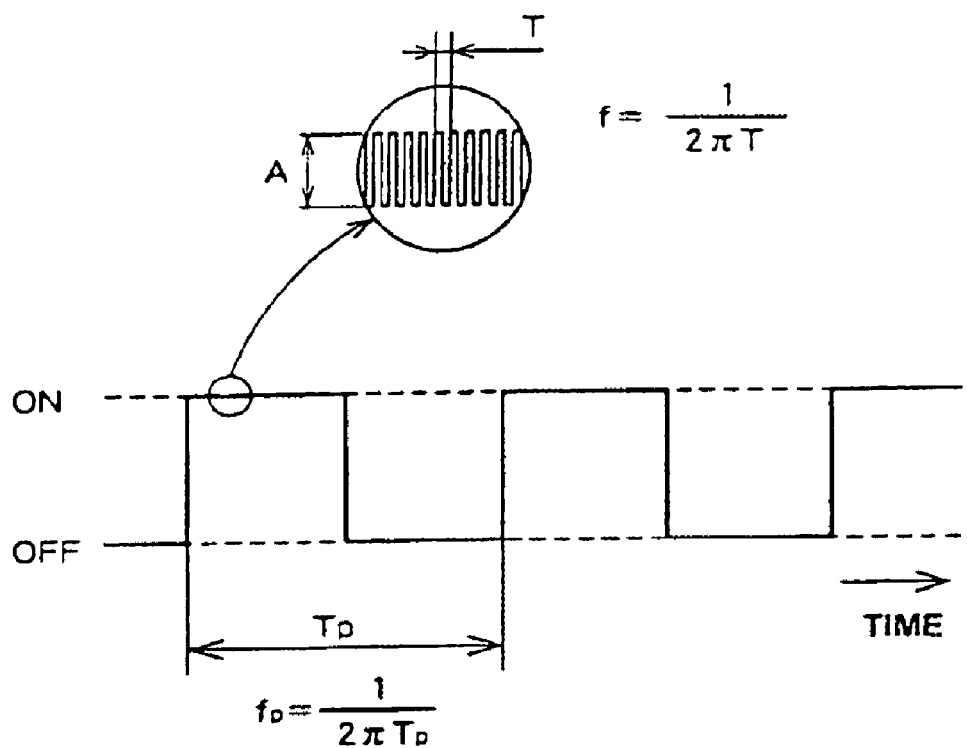
FIGS. 4a–4b is an explanatory diagram showing a voltage waveform applied to an oscillation mechanism by an oscillation mechanism drive circuit of the apparatus for controlling the movement of a specimen according to the embodiment of the present invention.

An embodiment which applies the apparatus for controlling the movement of a specimen according to the present invention to the control of the movement of a cell will be described with reference to the drawings. FIG. 1 shows a standing wave vibration of a vibrator and the resulting a flow of a medium and the movement of specimens, FIG. 2 shows a schematic configuration of the apparatus for controlling the movement of the specimen, FIG. 3 shows a schematic configuration of a manipulator, and FIG. 4 shows a voltage waveform to be applied to an oscillation mechanism.

First, a principle of the control of the position of a specimen in this embodiment will be described. FIG. 1 shows a state that a vibrator 11 (e.g., a probe section 11b) is oscillated in a medium 30, and a standing wave vibration V, e.g., vertical vibration, is generated at a tip of the vibrator 11 which is immersed in the medium 30. It was found through research conducted by the present inventors that when the vibrator 11 vibrates with the standing wave vibration V having at least one node (N1, N2), the following phenomenon is caused.

(I) Specimens S in the medium 30 move from the periphery of the vibrator 11 toward the nodes (N1, N2) of the standing wave vibration V and remain at positions in the vicinity of the surface of the nodes (N1, N2).

Utilizing the above characteristic, in this embodiment the vibrator 11 generates a standing wave vibration V having at least one node (N1, N2) to capture the specimens S in the medium 30, in the positions in the vicinity of the surface of the node (N1, N2) Here, positions where the specimens S are captured can be controlled freely through variable control of the vibration mode of the standing wave vibration V, and the specimens S can be controlled to a desired movement route or moving speed through variable control of vibration parameters (e.g., frequency, amplitude, intermittent frequency) of the standing wave vibration V.

The present inventors also found that the following phenomenon is observed when the vibrator 11 is vibrating at the standing wave vibration V having at least one node (N1, N2) as described above.

(II) The specimens S which are caught in the positions in the vicinity of the surface of the nodes (N1, N2) of the standing wave vibration V are rotated in these positions by the standing wave vibration V.

Utilizing the above characteristic, in the present embodiment the specimens S, which are captured in the positions in the vicinity of the surface of the nodes (N1, N2), are rotated by the standing wave vibration V. The specimens S can then be controlled to rotate in a desired rotating direction or at a desired rotational speed using variable control of the vibration parameters (e.g., frequency, amplitude, intermittent frequency) of the standing wave vibration V. Thus, the movement and/or orientation of the specimens S can be controlled as desired. As shown in FIG. 1, the specimens S at the adjacent nodes (N1, N2) rotate in different directions.

The specimen movement control apparatus 1, which freely controls the movement of the specimens S according to the aforementioned principle has a manipulator 10 and a control unit 20 as shown in FIG. 2. The manipulator 10 has a vibrator 11, an oscillation mechanism 12 for oscillating the vibrator 11, and a support section 13 for supporting the vibrator 11 as shown in FIG. 3. The vibrator 11 in turn has a vibrator base 11a, e.g., a metal tube, having the oscillation mechanism 12, a probe section 11b, e.g., a glass tube, and a tip of which is immersed in the medium 30, all connected by a joint section 11c, e.g., a rod member.

The probe section 11b is detachably fitted to the vibrator base 11a at the joint section 11c. A plurality of probe sections 11b can be exchangeably fitted to the joint section 11c. The vibration mode of the vibrator 11 is variable depending on a shape or a material of the vibrator 11. Therefore, when the vibrator 11 is configured to have a detachable component (e.g., the probe section 11b) with a different shape or material, the movement of the specimen S can be controlled by an appropriate vibration mode according to the characteristic (e.g., a size, mass or the like of the specimen S) of the specimen S or the characteristic (e.g., a viscosity or the like) of the medium 30. Specifically, the joint section 11c and the probe section 11b correspond to a vibration mode variable mechanism which changes the vibration mode of the vibrator 11 by exchanging a component (e.g., the probe section 11b) of the vibrator 11. The vibrator 11 of this embodiment has another component (e.g., the probe section 11b) which is detachable to the component, e.g., the vibrator base 11a, having the oscillation mechanism 12. Thus, it is easy to change the shape of the vibrator 11 and the vibration mode of the vibrator 11 while keeping the state of the oscillation mechanism 12 fitted to the vibrator 11.

The oscillation mechanism 12 is fixed to the vibrator 11, e.g., the vibrator base 11a. In this embodiment, the oscillation mechanism 12 is, for example, a cylindrical piezoelectric ceramic element which has a similar cylindrical detection element 12b fitted to surround a cylindrical oscillator 12a, and it is tightly fitted to surround the exterior of the vibrator base 11a which is a metal tube. The oscillator 12a and the detection element 12b are connected to an oscillation mechanism drive circuit 22.

Next, the control unit 20 will be described. The control unit 20 has a control section 21, e.g., a CPU, for controlling the entire apparatus 1, the oscillation mechanism drive circuit 22, e.g., a pulse generator, for driving the oscillation mechanism 12, a memory section 23, e.g., a RAM/ROM, an input section 24 (e.g., a keyboard 24a, a speed adjustment knob 24b, a movement/stop changeover switch 24c), and an output section 25, e.g., a display.

The control section 21 controls vibration of the oscillation mechanism 12 by controlling the oscillation mechanism drive circuit 22, to cause the vibrator 11 generate a standing wave vibration having at least one node. Specifically, the control section 21 corresponds to the vibration control mechanism. More specifically, the control section 21 controls the vibration of the oscillation mechanism 12 by controlling a pulse voltage (e.g., a pulse voltage shown in FIG. 4) which is applied from the oscillation mechanism drive circuit 22 (e.g., a pulse generator) to the oscillation mechanism 12.

Figure 4B:
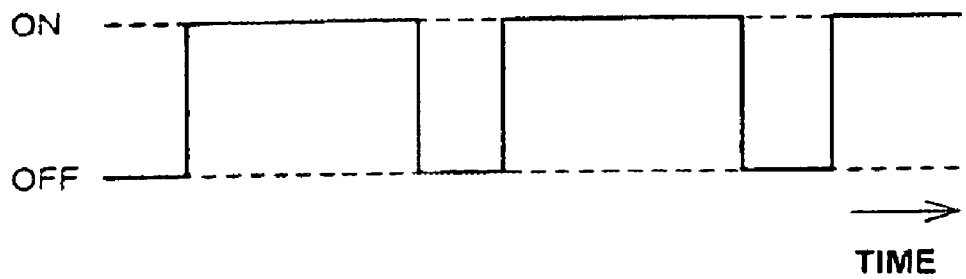

By employing the configuration described above, the control section 21 is able to change a frequency $f (=1/(2\pi T)$, T: cycle) of the applied voltage. This frequency f substantially corresponds to the vibration frequency of the vibrator 11, so that the vibration mode of the vibrator 11 is changed. In other words, the control section 21 corresponds to the vibration mode variable mechanism. The higher the frequency f, the greater will be the number of nodes. The control section 21 adjusts the amplitude A of the applied voltage so to adjust a moving speed (e.g., a moving speed or a rotational speed) of the specimen S in the medium 30. The higher the amplitude A of the applied voltage (namely, the vibration of the vibrator 11 has higher amplitude), the faster will be the moving speed of the specimen S. Additionally, the control section 21 periodically switches the applied voltage ON or OFF with pulsed intermittency (i.e., the vibration of the vibrator 11 is intermittently generated) to control a frequency fp (=1/(2πTp), Tp: one cycle of intermittence/stop, hereinafter the frequency fp will be called as an intermittent frequency fp) for switching the intermittence periodically and a ratio between a vibrating period and a vibration stopping period (hereinafter called as the intermittent duty ratio). The higher the intermittent frequency fp, the faster is the moving speed or the rotational speed. Additionally, the moving speed of the specimen S becomes faster as the vibrating period becomes longer (as the intermittent duty ratio is higher). In other words, when the applied voltage to the oscillation mechanism 12 has a waveform as shown in FIG. 4(b), the specimen S has a moving speed faster than that shown in FIG. 4(a).

The memory section 23 stores the vibration parameters (the vibrator 11 [e.g., the probe section 11b], vibration frequency, amplitude or intermittent frequency) for each treating condition (e.g., a type, size and mass of the specimen S to be treated or a medium for treating) of the specimen S. Thus, the control section 21 reads appropriate vibration parameters according to the treating conditions and can quickly and accurately control the vibration of the vibrator 11 and, therefore, the movement of the specimen S.

The input section 24, for example the keyboard 24a, inputs and sets the treating conditions, the vibration parameters, and the like. According to the input through the input section 24, the control section 21 controls each section of the apparatus 1. The speed adjustment knob 24b inputs an instruction regarding a moving speed or a rotational speed of the specimen S to the control section 21. More specifically, the control section 21 controls, for example, an intermittent frequency so as to change the moving speed or the rotational speed of the specimen S according to the amount a the knob 24b is turned from its neutral position NP. The memory section 23 stores the intermittent frequency at the neutral position NP and, when the knob 24b is turned in a clockwise direction from the neutral position NP, the control section 21 increases the intermittent frequency to higher a level higher so as to increase the moving speed of the specimen S, and when the knob 24b is turned in a counterclockwise direction, the control section 21 lowers the intermittent frequency so as to slow the moving speed of the specimen S. The movement/stop changeover switch 24c switches movement/stop of the movement or rotation of the specimen S by manual operation for example. More specifically, this switch 24c may be configured as a push button, for example,and the vibrator 11 may vibrate when the button is depressed and cease vibrating and when the button is no longer pushed. In other words, the control section 21 switches on and off oscillation of the vibrator 11 according to the input operation of the switch 24c. Therefore, the operator can operate the switch 24c to stop the movement of the specimen S in a desired position or orientation. The output section 25, for example a display, outputs, for example displays, the treating condition or the vibration parameters.

Figure 5:
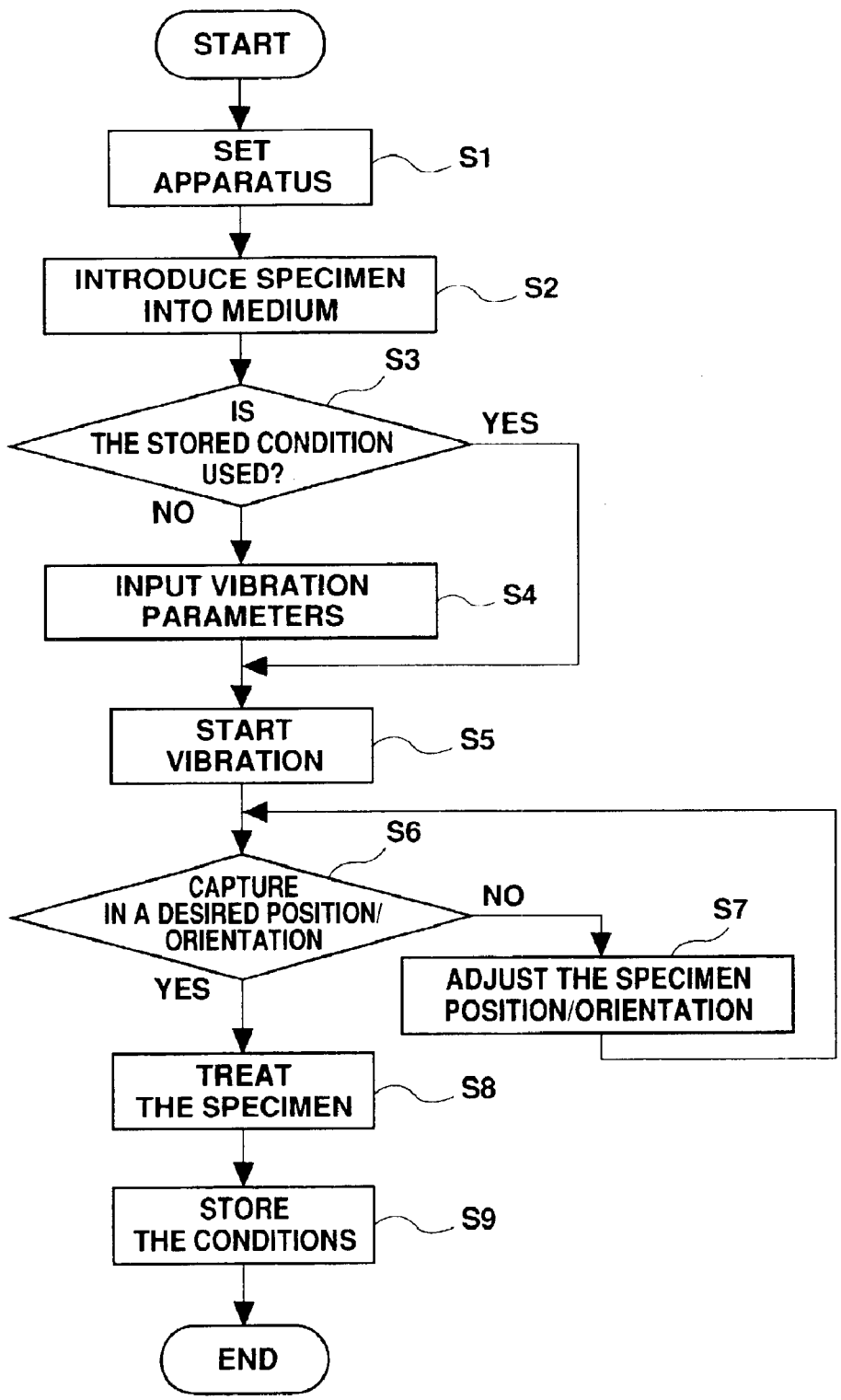
FIG. 5 is a flowchart showing a method for treating a specimen using the apparatus for controlling the movement of a specimen according to the embodiment of the present invention.

Next, a specimen treating procedure using the specimen movement control apparatus according to this embodiment will be described. FIG. 5 is a flowchart showing the specimen treating procedure.

First, the specimen movement control apparatus 1 is set (apparatus setting preparation step S1). In this step S1, the vibrator 11 is fitted to the specimen movement control apparatus 1, and the probe section 11b is fitted to the joint section 11c. As the vibrator 11 and the probe section 11b fitted here, those which generate an appropriate vibration mode depending on the specimen S and the medium 30 are selected.

Then, the medium 30 is poured into a vessel, and the specimen S is placed in the medium 30 (step S2 for placing the specimen into the medium).

The display 25 can display the past treatment conditions or vibration parameters stored in the memory section 23. For example, it may judged by the operator from the displayed results whether the stored condition setting is used or not (use condition selection step S3),and, when the stored condition setting is not used, vibration parameters are input through the input section 24, e.g., the keyboard 24a (vibration parameter input step S4). When the stored condition setting is used, the control section 21 obtains the vibration parameters of the condition setting from the memory section 23 according to the input about it from the input section 24, e.g., the keyboard 24a.

Next, the control section 21 begins oscillation of the vibrator 11 (vibration start step S5). For example, it is judged by observing through a microscope whether the specimen S is caught in a desired position and/or orientation (step S6 for judging capture in a desired position/orientation), and when the specimen S is not caught in a desired position/ orientation, an instruction is input from the input section 24, e.g., the keyboard 24a, the speed adjustment knob 24b, or the movement/stop changeover switch 24c, and the position and/or orientation of the specimen S is adjusted (specimen position/orientation adjustment step S7). More specifically, the moving speed or the rotational speed of the specimen S is adjusted by operating the speed adjustment knob 24b for example, and the movement/stop of the specimen S is switched by operating the movement/stop changeover switch 24c to adjust the specimen S to a desired position and/or orientation. The capturing position can be moved along the surface of the vibrator 11 or a flow of the medium 30 around the vibrator 11 can be changed by inputting a change instruction for the vibration frequency of the vibrator 11 through the keyboard 24a, for example.

After capturing in a desired position and/or orientation is completed, the treatment of the specimen S, e.g., microinjection into the cell nucleus, is performed. In this embodiment, because the specimen S can be captured in a position and a orientation suitable for its treatment, the treatment can be performed easily and quickly with high accuracy. For example, when an egg cell is used as the specimen S in the microinjection, the vibration of the vibrator 11 may be controlled to adjust the orientation of the egg cell so to direct the nucleus of the egg sell toward the injector.

Before the power of the specimen movement control apparatus 1 is turned off, the control section 21 stores the vibration parameters used for controlling the position and/or orientation of the specimen in the memory section 23 (control condition storing step S9). Thus, when a subsequent treatment is performed under the same condition (e.g., the used specimen or medium 30), the position and/or orientation of the specimen S can be controlled still more quickly and more accurately using the stored data.

Next, a method for removing the contents of a cell as the specimen by the specimen movement control apparatus 1 will be described. FIG. 6 is an explanatory diagram showing a state of the cell treated by this method.

Figure 6A:
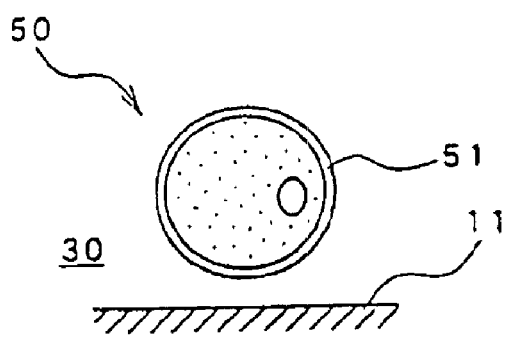
FIGS. 6a–d is an explanatory diagram showing a method for removing the contents of a cell by means of the apparatus for controlling the movement of a specimen according to the embodiment of the present invention.
Figure 6B:
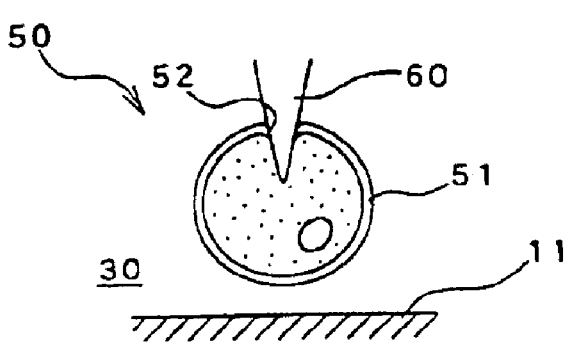
Figure 6C:
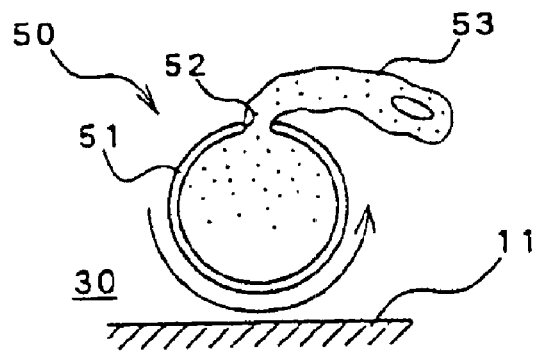
Figure 6D:
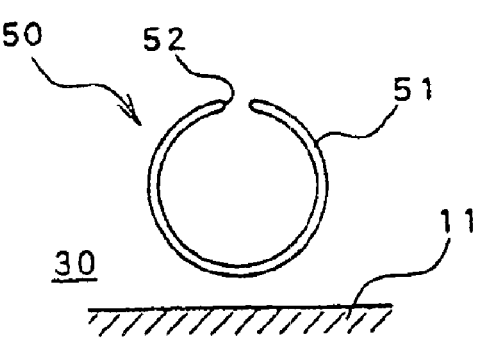

First, the above-described steps S1 to S7 are performed to capture a specimen having contents, e.g., a cell 50, in a desired position and orientation (FIG. 6(a)). Then, a needle 60 is inserted into a shell, e.g., cell membrane 51, of the specimen to form a hole 52 (cell membrane opening step; FIG. 6(b)). According to an instruction input from the input section 21, the cell 50 is rotated (cell rotation step; FIG. 6(c)). When the cell 50 is rotated, the contents 53 of the cell 50 are discharged out of the cell 50 by centrifugal force to the medium 30 through the hole 52. By the above method, the shell, e.g., the cell membrane 51, having the contents 53 removed can be obtained easily and quickly (FIG. 6(d)). By appropriately setting the rotational speed of the cell in its rotation step depending on the treating conditions (e.g., a type, size and mass of the cell 50, a size of its contents [e.g., a nucleus] or a viscosity of the contents), the contents 53 can be removed more quickly and more accurately.

The present invention is not limited to the above-described embodiment. For example, a mechanism which has a member in contact with the vibrator and can change its contact position may be disposed as the vibration mode variable mechanism. By configuring as described above, the vibration mode of the vibrator can also be controlled variably. The specimen movement control apparatus may also be provided with an image pickup section for imaging of the specimen and a position/orientation judgment section which judges whether the specimen is captured in a desired position or orientation according to the image taken by the image pickup section, and the control of the specimen to a desired position/orientation may be performed automatically according to the determined position/orientation.

INDUSTRIAL APPLICABILITY

As described above, according to the specimen movement control apparatus, method, and the specimen treating method according to the present invention, the movement of a specimen in the field of biotechnology can be controlled freely by making the vibrator disposed in the medium generate a standing wave vibration having at least one node, so that, for example, a very small specimen such as a cell can be treated easily, quickly, and with a high accuracy.

What is claimed is:

1. An apparatus for controlling the movement of a specimen, comprising:

a vibrator which vibrates a medium including the specimen therein;

an oscillation mechanism which is connected to the vibrator causes the vibrator to vibrate; and a vibration control mechanism which controls the oscillation mechanism to make the vibrator generate a standing wave vibration having at least one node, where the vibrator rotates the specimen in a desired manner, wherein the vibration control mechanism causes the vibrator to vibrate intermittently.

2. The apparatus for controlling the movement of a specimen according to claim 1, further comprising a vibration mode variation mechanism which can change the vibration mode of the vibrator.

3. The apparatus for controlling the movement of a specimen according to claim 1, wherein the vibrator is disposed in the medium.

4. A method for controlling the movement of a specimen, comprising:

placing the specimen in a medium; and causing a vibrator disposed in the medium to generate a standing wave vibration having at least one node so as to capture the specimen by the node of the standing wave vibration in the vicinity of the surface of the vibrator so as to rotate the specimen at a desired speed or in a desired orientation.

5. A method for manipulating a specimen, comprising:

placing the specimen in a medium;

causing a vibrator disposed in the medium to generate a standing wave vibration having at least one node so as to capture the specimen at the node of the standing wave vibration in the vicinity of the surface of the vibrator as to rotate the specimen at a desired speed or in a desired orientation; and performing a prescribed treatment of the captured specimen.

* * * * *